United States Patent [19]

Corsello et al.

[11] Patent Number: 4,997,654
[45] Date of Patent: Mar. 5, 1991

[54] METHOD FOR INCREASING SALIVATION FOR XEROSTOMIA PATIENTS

[75] Inventors: Vincent Corsello, Cedar Knolls; Michael Glass, Fair Lawn; Norton Ross, Randolph; Joseph Hohclick, Hopatcong, all of N.J.; Kenneth P. Bilka, Floral Park, N.Y.

[73] Assignee: Warner-Lambert Company, Morris Plains, N.J.

[21] Appl. No.: 393,422

[22] Filed: Aug. 14, 1989

[51] Int. Cl.$^5$ .............................................. A61K 9/68
[52] U.S. Cl. .................................... 424/440; 424/441; 424/48
[58] Field of Search .......................... 424/440, 441, 48

[56] References Cited

U.S. PATENT DOCUMENTS

| Re. 30,197 | 1/1980 | Klose et al. | 426/3 |
| Re. 31,954 | 7/1985 | Fine et al. | 424/58 |
| 3,899,593 | 8/1975 | Hammond et al. | 426/3 |
| 4,000,320 | 12/1976 | Klose et al. | 426/3 |
| 4,065,578 | 12/1977 | Reggio et al. | 426/3 |
| 4,088,788 | 5/1978 | Ream et al. | 426/3 |
| 4,127,677 | 11/1978 | Fronczowski et al. | 426/5 |
| 4,284,650 | 8/1981 | Goupil | 426/5 |
| 4,568,537 | 2/1986 | Hoerman et al. | 424/48 |

OTHER PUBLICATIONS

Markovic, N., Abelson, D. C., Mandel, I. D., Gerodontology, V7, N2, (1988), ISSN 0734-0664, pp. 71-75.
Gilpin, J. L., JDH, Mar.-Apr. 1989, pp. 111-114, Laclede Research Laboratories, Professional Products Literature.

Primary Examiner—Thurman K. Page
Assistant Examiner—James M. Spear
Attorney, Agent, or Firm—Daniel A. Scola, Jr.; Richard S. Bullitt

[57] ABSTRACT

A method for treating xerostomia which comprises chewing gum or candy containing from 4 to 70 weight percent xylitol therein.

21 Claims, 2 Drawing Sheets

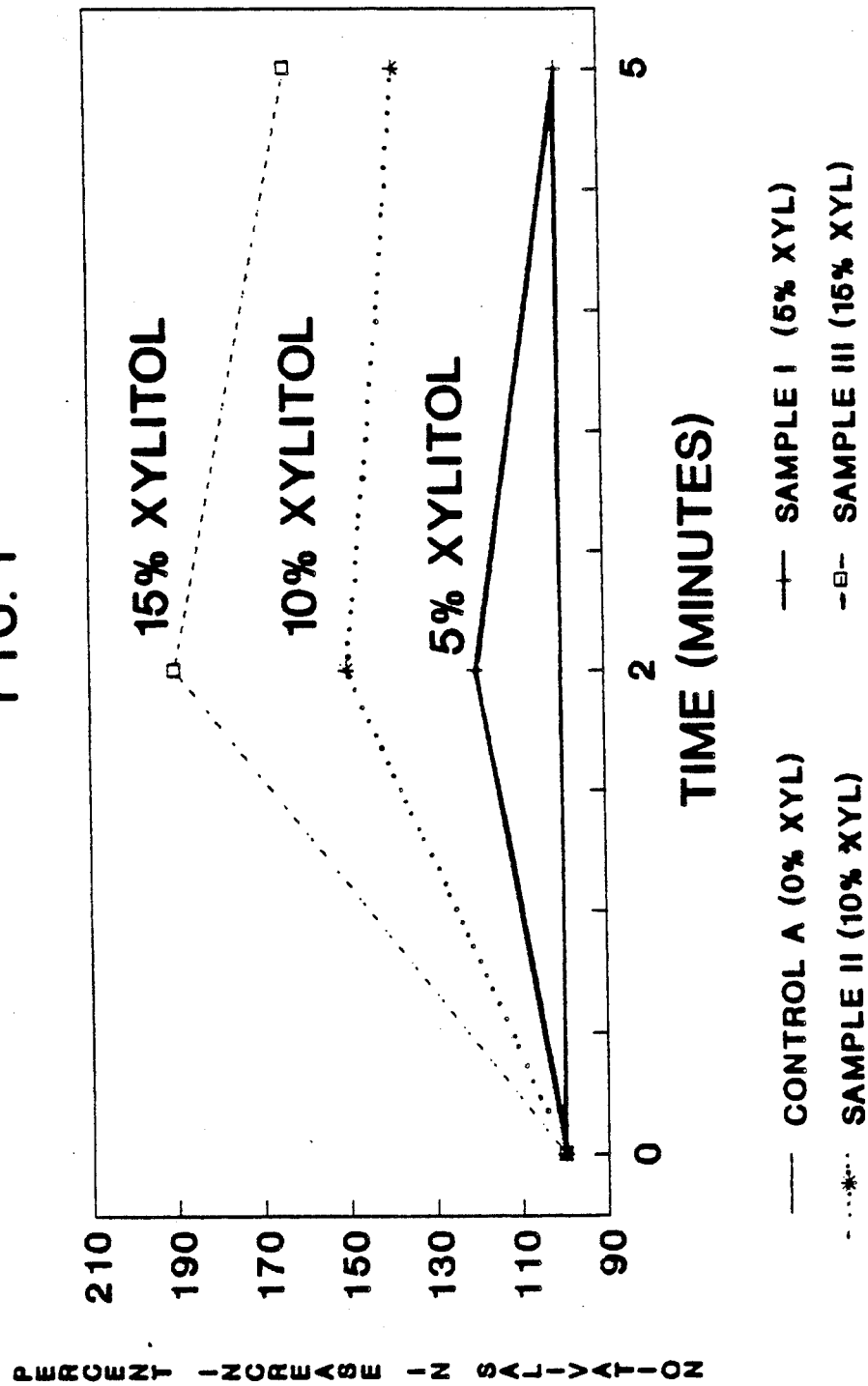

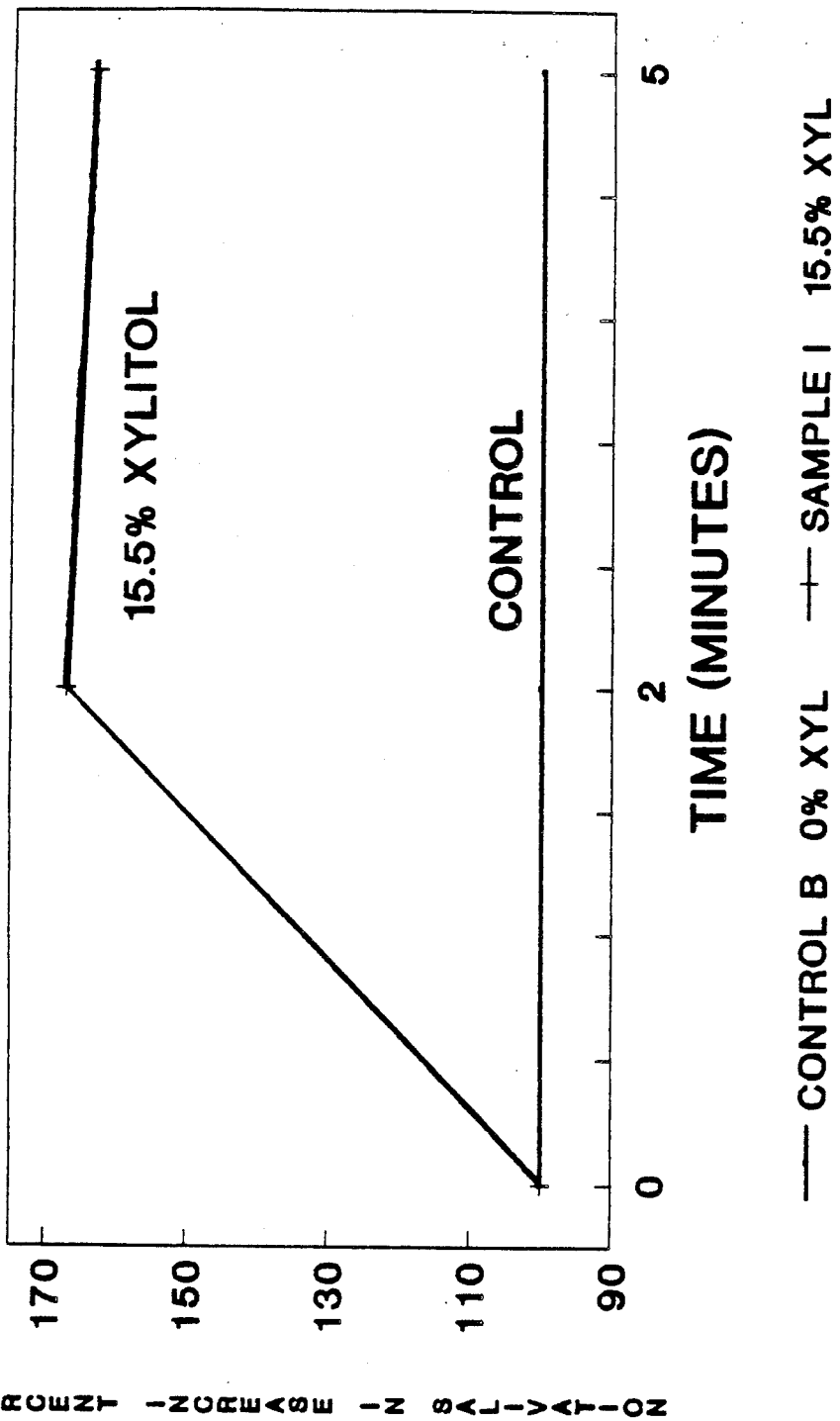

METHOD FOR INCREASING SALIVATION FOR XEROSTOMIA PATIENTS

BACKGROUND OF THE INVENTION

1. Field of the Invention

This invention relates to a method for increasing salivation for the treatment of xerostomia and more particularly to increasing salivation by means of a chewing gum or confectionery composition containing xylitol.

2. Description of Related Art

Xerostomia, dry mouth syndrome or hyposalivation, has been defined functionally as a reduction of unstimulated salivary flow by greater than fifty percent as described by J. L. Gilpin in JDH, March–April, 1989, pp. 111–114. Xerostomia is a subjective clinical symptom characterized by a less than a normal amount of saliva with no apparent boundary between normal and abnormal. Saliva is a fluid mixture containing secretions from the salivary glands (parotid, submandibular, and sublingual), and many smaller minor salivary glands embedded in the submucosa of the cheeks, lips, hard and soft palates, and tongue. Because of its frequent occurrence in the elderly xerostomia was formerly thought to be a normal part of the aging process. Subsequent studies, however, indicate that xerostomia occurs in all age groups. Systemic diseases, medications, radiation therapy, and/or immunosuppression are among the main causes of dry mouth in the elderly. Clinical signs of xerostomia include dry, smooth, shiny mucosa, epithelial atrophy, inflammatory fissuring, especially of the tongue, and rampant caries, particularly of the cervical third of the teeth. Xerostomic patients may experience symptoms such as burning sensations due to fungal infection, inflammation of the tongue, and/or glossodynia or painful tongue. Patients may complain of difficulty with speech, swallowing, or denture retention. Xerostomia patients may even experience taste alterations and report that food tastes bland and papery, or they may experience salty or other unpleasant tastes. Normal saliva contains electrolytes of sodium, potassium, calcium, chloride, bicarbonate, and inorganic phosphate. Some of these components have specific taste properties, such as sodium (salty), and potassium (bitter/salty).

Various therapeutic measures have been recommended for patients experiencing xerostomia. Some of these include frequent rinsing with saline solutions to keep oral tissue moist and healthy. Additionally, fluoride rinses and topical gels have also been used to protect existing dental enamel and avoid root caries. Besides rinses, artificial saliva and salivary substitutes have been proposed as a palliative treatment for patients with non-functional glandular tissue, which preparations have a viscosity and electrolyte composition that approximates whole saliva. The use of mints and chewing gum have also been recommended to patients with non-atrophied glandular tissue, including gustatory stimulants such as lozenges or masticatory stimulants such as sugar-free chewing gum. See MARKOVIC, et al., Gerodontology, Vol. 7, Number 2, 1988 p. 71–75.

Saliva stimulating chewing gum compositions have been reported in the past. For example, U.S. Pat. No. 4,088,788 issued May 9, 1978 to R. L. REAM, et al., discloses such a chewing gum composition. The composition of Ream et al. comprises at least 3 percent by weight of an organic acid in combination with acid saccharin as the active agents for stimulating salivation. The gum further contains gum base, sodium and potassium salts, flavoring, emulsifiers, softeners and sweeteners.

U.S. Pat. No. 4,568,537 issued on Feb. 4, 1986 to K. C. HOERMAN, et al., also discloses a chewing gum composition containing an organic acid, e.g. adipic acid, as the active ingredient for stimulating salivary flow upon chewing of the gum. Salivation is said to be stimulated to an extent in excess of that required to neutralize the acid. Failure to neutralize the acid would be detrimental to the user. The gum preferably contains a sugarless sweetener which can be a water-soluble bulking agent present in an amount from about 30% to 65% by weight of the chewing gum and may comprise a sugar alcohol selected from sorbitol, mannitol and xylitol or mixtures thereof.

U.S. Pat. No. 4,284,650 issued Aug. 18, 1981 to J. J. GOUPIL, is directed to an anticaries chewing gum composition comprising an alkaline earth free gum base, a water-soluble fluoride and 10–53% xylitol mixed with sorbose or sorbitol. Fluorine is taught to be the active anticaries agent, xylitol, sorbose and sorbitol are used merely as sweeteners.

U.S. Pat. No. 4,127,677 issued Nov. 28, 1978 to P. O. FRONCZOWSKI, et al., discloses a xylitol coated chewing gum for providing an intense instantaneous cooling effect.

U.S. Pat. No. 3,899,593 issued Aug. 12, 1975 to J. E. HAMMOND, et al., is directed to chewing gum containing large quantities (>50%) of xylitol for imparting a pleasant cooling effect.

U.S. Pat. No. 4,000,320 issued Dec. 28, 1976 to KLOSE, et al., discloses a sugar sweetened chewing gum composition which comprises gum base, flavor and sugar wherein the improvement comprises adding xylitol to the chewing gum composition in amounts less than 50% by weight of total gum composition which is effective to extend the storage stability of the gum. This patent was reissued as U.S. Pat. No. 30,197 on Jan. 22, 1980 wherein the xylitol amount was limited to less than 10% by weight of the total gum composition.

U.S. Pat. No. 4,065,578 issued Dec. 27, 1977 to REGGIO, et al., discloses a sugarless chewing gum in the form of a soft, moist, continuous cohesive gum, which comprises gum base, xylitol as a bulk filler and sweetener, and a hydrocolloid selected from the group consisting of xanthan gum or an alginate derivative of kelp as a binder to facilitate formation of the soft, moist, continuous cohesive gum, said hydrocolloid being present in an amount within the range of from about 0.03 to about 1.0% by weight of said chewing gum and wherein said xylitol is preferably present in an amount within the range of from about 50 to about 70% by weight.

SUMMARY OF THE INVENTION

The present invention relates to a method for treating xerostomia and more particularly a method for treating xerostomia with a specially formulated confectionery or chewing gum composition containing about 4% to about 70% by weight xylitol. The chewing gum formulations of the invention also contain a sugar alcohol in amounts of about 40% to about 85% by weight wherein the sugar alcohol is sorbitol, mannitol and mixtures thereof.

The chewing gum formulations of this invention are particularly suited for treating xerostomia derived from a variety of causes. More particularly it relates to a xylitol containing confectionery or chewing gum product for treating xerostomia which is caused by:

(a) factors affecting the brain's control of salivation such as emotions, neurosis, and organic diseases;

(b) factors affecting the automatic outflow pathway such as encephalitis, tumors, cerebrovascular accidents and medications;

(c) factors affecting the salivary gland such as Sjogren's syndrome, and irradiation; and (d) factors affecting fluid or electrolyte balance such as dehydration, diabetes, cardiac failure, hypertension, thyroid disease, and hormone dysfunction.

It should be understood that while the use of xylitol in confectionery and chewing gum products is old, its use was limited as a sweetener or to impart a cooling sensation. There was no appreciation in the art that xylitol was effective in promoting salivation useful for the treatment of xerostomia.

BRIEF DESCRIPTION OF THE DRAWINGS

FIG. 1 demonstrates the percentage increase in salivation from the formulations set forth in Example 1.

FIG. 2 demonstrates the percentage increase in salivation from the formulations set forth in Example 2.

DETAILED DESCRIPTION OF THE INVENTION

As discussed above, xerostomia is a condition wherein a person suffers from dry mouth due to an insufficient flow of saliva. Lack of salivation, besides making the oral cavity uncomfortably dry, decreases to some degree, the efficiency of digestion and also creates an environment in the oral cavity which makes it prone to gum and tooth disease.

It has been now unexpectedly discovered that xylitol when applied to the oral cavity in effective amounts and for effective periods of time promotes and stimulates salivation. This effect of xylitol has not been previously appreciated.

Xylitol is a 5-carbon sugar alcohol that occurs naturally in raspberries, strawberries, yellow plums, cauliflower, spinach, and several other plants. Although it is widely distributed, the low concentrations of xylitol within plants makes it uneconomic to extract the substance directly. Consequently, xylitol must be commercially produced from xylan or xylose-rich precursors by way of chemical, enzymatic, or microbiological conversion. The most commonly used and highest-yield xylan sources are birch tree chips. Other appropriate starting materials include beech and other hardwood chips, almond and pecan shells, cottonseed hulls, straw, cornstalks (maize), and corn cobs. These xylan sources are routinely converted to xylitol by: hydrolysis of xylan to d-xylose; reduction of xylose to xylitol by pressure hydrogenation in the presence of a nickel catalyst; and purification and crystallization of xylitol end-products. Xylitol appears as a crystalline compound which possesses a sweetness level of about 90% that a sucrose and xylitol is metabolized in the body to glycogen by way of the pentose-phosphate pathway and is thus safely consumed by diabetics.

Generally, the preferred method for introducing the xylitol into the oral cavity is by means of an edible product such as chewing gum or confectionery. Using these types of products xylitol can be released into the oral cavity over a period of time, typically on the order of about 1 to 5 minutes or longer, which is sufficient to stimulate and sustain salivation. When employed in a chewing gum or confectionery base, the xylitol must be present in an amount of at least 4% by weight of the chewing gum or confectionery product to be significantly effective. Amounts below about 4% are not effective at stimulating adequate salivary flow. Typically, xylitol is present in an amount of from about 4% to about 70% by weight of the edible product. Amounts above about 70% should not be employed since they produce products that are too soft which are not able to maintain sufficient residence time in the oral cavity to be effective. A preferred amount is from about 4% to about 25% and more preferably from about 5% to about 15% by weight of the final product.

In formulating a suitable chewing gum or candy for use in the treatment of xerostomia, in addition to the required chewing gum or candy base and effective quantity of xylitol, the chewing gum or confectionery contains a sugar alcohol in the amount of about 40% to about 85% by weight and preferably from about 40% to about 60% by weight of the final product. The use of sugarless products is preferred to reduce cariogenic difficulties.

In addition to the foregoing components the products may also contain one or more of any of the conventional additives found in such formulations as are well known in the art. Typical conventional additives, for example, include softeners, emulsifiers, flavorants, sweeteners, colorants, plasticizers, humectants and binders.

The chewing gum compositions of this invention are those which are generally known in the art, such compositions contain a gum base and a sweetening agent. A chewing gum base useful in the instant invention may be any water-insoluble gum base well known in the art. Illustrative examples of suitable polymers in gum bases include both natural and synthetic elastomers and rubbers. For example, those polymers which are suitable in chewing gum bases include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene, and polyvinylacetate and mixtures thereof, are particular useful.

The amount of chewing gum base employed will vary greatly depending on various factors such as the type of base used, consistency desired and other components used to make the final product. In general, amounts of chewing gum base up to about 56% by weight of the final chewing gum composition are acceptable with preferred amounts of about 11% to about 45% and most preferred amounts of about 15% to about 25% by weight.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of partially dimerized rosin, glycerol ester of polymerized rosin, glycerol ester of tall oil rosin, glycerol ester of wood rosin and partially hydrogenated wood rosin, and partially hydrogenated methyl ester of rosin and mixtures thereof. The solvent may be employed in an amount ranging from about 10% to about 75% and preferably about 45% to about 70% by weight of the gum base.

A variety of traditional ingredients used as plasticizers of softeners such as lanolin, stearic acid, sodium stearate, potassium stearate, glyceryl triacetate, glycerine and the like, may also be incorporated into the gum base to obtain a variety of desirable textures and consistency properties. These individual additional materials are generally employed in amounts up to about 30% by weight and preferably in amounts of from about 3% to about 7% by weight of the final gum base composition.

The chewing gum compositions employing the instant gum bases preferably contain sweetening agents in addition to the required xylitol. The sweetening agent may be selected from a wide range of materials including water-soluble agents, water-soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch or corn syrup alcohols such as sorbitol, mannitol and mixtures thereof, and natural sweeteners such as dehydrochalcone, glycyrrhizin and stevia rebaudiana (Stevioside).

B. Water-soluble artificial sweeteners such as the soluble saccharine salts, i.e., sodium or calcium saccharin salts, cyclamate salts, acesulfame-K and the like, the free acid form of saccharin, and the chlorinated sugar derivatives such as Sucralose.

C. Dipeptide based sweeteners such as L-aspartyl-L phenylalanine methyl ester and materials described in U.S. Pat. No. 3,492,131 and Alitame and the like. In general, the total amount of sweetener including the xylitol, will vary with the desired amount of sweetener selected for a particular chewing gum or confectionery product. This amount will normally be 4% to about 99% with from 0.01% to about 86% by weight of sweetener other than the xylitol when using an easily extractable sweetener. The water-soluble sweeteners described in category A above, are preferably used in amounts of about 25% to about 75% by weight, and most preferably from about 50% to about 65% of the final chewing gum composition, including xylitol which is also water soluble and can be up to 100% when used in confectionery products. In contrast, the artificial sweeteners described in categories B and C are used in amounts of about 0.005% to about 1.0% and most preferably about 0.05% to about 0.8% by weight of the final composition. These amounts are ordinarily necessary to achieve a desired level of sweetness independent from the flavor level achieved from flavor oils.

Natural and synthetic flavoring agents well known to the confectionery and chewing gum art may be added to the chewing gum compositions of the instant invention. These flavoring agents may be chosen from synthetic flavor oils and flavoring aromatics, and/or oils, oleo resins and extracts derived from plants, leaves, flowers, fruits and so forth, and combination thereof. Representative flavor oils include: spearmint oil, cinnamon oil, oil of wintergreen (methylsalicylate), peppermint oils, clove oil, bay oil, anise oil, eucalyptus oil, thyme oil, cedar leaf oil, oil of nutmeg, oil of sage, oil of bitter almonds, and cassia oil. Also useful are artificial, natural or synthetic fruit flavors, such as vanilla, and citrus oil, including lemon, orange, grape, lime and grapefruit and fruit essence including apple, pear, peach, strawberry, raspberry, cherry, plum, pineapple, apricot and so forth.

The amount of flavoring agent employed is normally a matter of preference subject to such factors as flavor type, gum base type and strength desired. In general, amounts of about 0.5% to about 3.0% by weight of the final chewing gum composition are usable with amounts of about 0.3% to about 1.5% being preferred and about 0.7% to about 1.2% being most preferred.

The emulsifiers may be selected from a wide range of compounds. Exemplary groups of compounds may be selected from fatty acid esters and mono and diglycerides. Specific compounds and their respective HLB (hydrophile-lipophile balance) values include glycerol monooleate (2.8); propylene glycol monostearate (3.4), glycerol monostearate (3.8), lecithin (4.2), and sorbitan monostearate (4.7).

The colorants useful in the present invention, include pigments such as titanium dioxide, and are incorporated in amounts of up to about 2% by weight, and preferably up to about 1% by weight. Colorants may also include dyes suitable for food, drug and cosmetic applications. These colorants are known as F.D.&C. dyes. The materials acceptable for the foregoing spectrum of use are preferably water-soluble. Illustrative examples include indigo dye, known as F.D.&C. Blue No. 2, which is the disodium salt of 5,5'-indigotin-disulfonic acid. Similarly, the dye known as F.D.&C. Green No. 1, comprises a triphenylmethane dye and is F.D.&C. and D.&C. colorants and their corresponding chemical structures may be found in the Kirk-Othmer Encyclopedia of Chemical Technology, in Volume 5, at page 857-884.

The chewing gum compositions of the present invention may be prepared into all the varies end forms known commercially, including slab form, stick form, cube form and center-filled form. While both sugar and sugarless chewing gums are contemplated within the scope of this invention, sugarless forms are preferred. All of the techniques associated with the preparation of the products in these forms are well known and the present method may vary somewhat depending upon the specific end product to be manufactured.

The following chewing gum formulations are exemplary formulations useful in the present invention. These formulations are merely illustrative based upon weight of the final composition.

| Sugarless Slab Gums with Xylitol | |
|---|---|
| Ingredient | Range |
| Gum Base | 18%–45% |
| Lecithin | 0.1%–1.0% |
| Acetylated Monoglycerides | 0.1%–1.0% |
| Sorbitol | 15%–75% |
| Mannitol | 5%–75% |
| Xylitol | 4%–70% |
| Glycerin | 7%–18% |
| Artificial Sweetener(s) | 0.0005%–1% |
| Flavor | 0.5%–3% |

| Sugarless Center filled Gum | |
|---|---|
| Gum Ingredients | Range (wt. %) |
| Gum Base | 17%–45% |
| Gum Arabic Solution* | 5%–12% |
| CMC Solution** | 0.5%–10% |
| Mannitol | 0%–56% |
| Sorbitol | 10%–75% |
| Xylitol | 4%–56% |
| Artificial Sweetener | 0.0005%–1% |
| Flavor | 0.5%–2% |

-continued

| Center Fill Ingredients | |
|---|---|
| CMC solution** | 11.86% |
| Flavor | 0.11% |
| Artificial Sweetener | 0.03% |

*Composed of Gum Arabic Powder and Water
**Composed of Sodium Carboxymethyl Cellulose, Glycerin 70% Sorbitol Solution The confectionery products of this invention are formulated by conventional means. In general, a hard confectionery has a base composed of a mixture of cane or beet sugar, polyhydric alcohols and glucose syrup, which are present in the final confectionery in amounts of between about 5% and about 99% by weight of the final composition and low moisture levels, e.g., from 0.5 to 1.5%. Such confectionery may be routinely prepared by conventional methods, such as those involving fire cookers, vacuum cookers and scraped-surface cookers also referred to as high speed atmospheric cookers.

Fire cookers involving the traditional method of making candy base, may be used. In this method the desired quantity of sugar is dissolved in water by heating in a kettle until the sugar dissolves. Corn syrup or an invert sugar is then added and cooking continued until a final temperature of 145° to 165° is achieved. The batch is then cooled and worked as a plastic-like mass to incorporate additives.

A high-speed atmospheric cooker uses a heat-exchange surface. Processes using it involve spreading a film of candy on a heat exchange surface, and heating the candy to 165° to 170° C. in a few minutes. The candy is then rapidly cooked to 100° to 120° C. and worked as a plastic-like mass enabling incorporation of the additives, such as flavor, color, acidulents and medicaments. It is at this point that the inventive cooling compositions may be blended into the candy.

In vacuum cookers, the sugar and corn syrup are boiled to 125° to 132°, C. vacuum applied, and additional water is boiled off without extra heating. When cooking is complete, the mass is a semi-solid, having a plastic-like consistency. At this point, color, flavors, and additives are mixed in the mass by routine mechanical mixing operations.

The optimum mixing required to uniformly mix the flavor, color, and other additives during conventional manufacturing of confectionery is determined by the time needed to obtain a uniform distribution of the materials. Normally, mixing times of 4 to 10 minutes have been found acceptable.

Once the candy mass has been properly tempered, it may be cut into workable portions or formed into desired shapes. A general discussion of the composition and the preparation of hard confections may be found in H. A. Lieberman, Pharmaceutical Dosage Forms: Tablets Vol. 1 (1980), Marcel Dekker, Inc. at pages 339 to 469.

It should be mentioned that the apparatus useful in accordance with the present invention comprises those cooking and mixing apparatus well known in the confectionery manufacturing arts, and therefore, the selection of a specific apparatus will be apparent to the ordinary skilled artisan.

The xylitol containing composition of the invention are useful for treating the many causes for xerostomia. As discussed by Gilpin above these causes may be classified into four major groups.

Group one includes factors affecting the brain's control of salivation such as emotions, neurosis, and organic diseases. Group two includes factors affecting the automatic outflow pathway such as encephalitis, tumors, cerebrovascular.

The third group of factors affects the function of the salivary gland. These includes Sjogren's syndrome, obstruction and infection of the glands, tumors, aplasia, excision, and irradiation. Radiation-induced xerostomia occurs when salivary glands are subjected to radiation doses from 4,000 to 6,000 rads (radiation absorbed dose).

The last group of factors includes those affecting fluid or electrolyte balance. Some of these factors are dehydration, diabetes, cardiac failure, hypertension, thyroid disease, hormone dysfunction, Parkinson's disease, anemia, and the use of diuretics.

The following examples serve to provide further appreciation of the invention but are not meant in any way to restrict the effective scope of the invention. All percentages throughout the specification are by weight % of the final confectionery or chewing gum composition unless otherwise indicated and wherein all percentages will total 100% of ingredients in the final composition.

EXAMPLE I

This example demonstrates the preparation of slab type chewing gum compositions using various amounts of xylitol.

The formulations were prepared with the ingredients recited in Table I. The formulations were prepared by first melting the gum base at a temperature from 82° to 95° C. and mixing the gum base in a kettle with lecithin and acetylated monoglyceride until a homogenous mixture was obtained, approximately 2 minutes. To this mixture was added, the sorbitol, mannitol, xylitol and glycerin wherein mixing was continued for several minutes and thereafter the flavor and artificial sweeteners were mixed into the mixture for approximately 4 minutes.

The gum was then discharged and formed into slabs and cooled to room temperature.

In order to evaluate the chewing gum formulations a comparison was undertaken with a control which contained no xylitol but only sorbitol/mannitol. The xylitol was used to replace the sorbitol present in the formulation.

The final formulations were subjected to test panel studies with multiple panelists. The panelists chewed each piece and separately recorded their observations concerning the amount of increase in salivation experienced. The results are set forth in FIG. I which clearly demonstrates an enhanced salivation from the chewing gum containing xylitol as compared with the formulation containing merely sorbitol/mannitol. Further, the rate of salivation increased with increasing amounts of xylitol.

TABLE I

| Ingredient | Control A(wt. %) | Inventive Runs I(wt. %) | II(wt. %) | III(wt. %) |
|---|---|---|---|---|
| Gum Base | 24 | 24 | 24 | 24 |
| Lecithin | 0.5 | 0.5 | 0.5 | 0.5 |

TABLE I-continued

| Ingredient | Control A(wt. %) | I(wt. %) | Inventive Runs II(wt. %) | III(wt. %) |
| --- | --- | --- | --- | --- |
| Acetylated Monoglyceride | 0.35 | 0.35 | 0.35 | 0.35 |
| Sorbitol | 45.699 | 40.699 | 35.830 | 30.830 |
| Mannitol | 15.000 | 15.000 | 15.000 | 15.000 |
| Xylitol | 0.000 | 5.000 | 10.000 | 15.000 |
| Glycerin | 10.000 | 10.000 | 10.000 | 10.000 |
| Flavor | 1.700 | 1.700 | 1.700 | 1.700 |
| Encapsulated Sweetener | 2.751 | 2.751 | 2.751 | 2.751 |

EXAMPLE II

The procedure of Example I was repeated except that the formulation prepared was a centerfilled chewing gum composition set forth in Table II.

After the base was heated, the CMC solution, gum arabic solution and artificial sweetener were mixed into the gum base. After the remaining components were blended into the formulation, the formulation was extruded and centerfilled with the centerfill composition, and thereafter cut into chunks and cooled to room temperature.

As in Example I, each piece was subjected to test panel studies with multiple panelists. The results were likewise recorded separately and are summarized in FIG. 2.

Results of chew panels comparing the control (gum without xylitol) to gum with xylitol in effective quantities with regard to the degree of salivation, found the xylitol containing gums to induce greater salivation than the non-xylitol control.

The invention being thus described, it will be obvious that the same may be varied in many ways. Such variations are not to be regarded as a departure from the spirit and scope of the invention and all such modifications are intended to be included within the scope of the following claims.

TABLE II

| Ingredient | Control B(wt. %) | IV(wt. %) |
| --- | --- | --- |
| GUM | | |
| Gum Base | 18.3634 | 19.180 |
| Gum Arabic Solution | 7.3453 | 7.357 |
| CMC Solution | 4.5905 | 1.927 |
| Mannitol | 16.1190 | 0.000 |
| Sorbitol | 40.9150 | 42.914 |
| Xylitol | 0.0000 | 15.447 |
| Flavor | 1.2881 | 1.283 |
| Color | 0.1658 | 0.168 |
| Artificial Sweetener | 0.2254 | 0.224 |
| CENTER | | |
| CMC Solution | 10.8506 | 11.3568 |
| Flavor | 0.1090 | 0.1137 |
| Artificial Sweetener | 0.0278 | 0.0295 |

What is claimed is:

1. A method for treating xerostomia; which comprises:
    introducing into the oral cavity an edible composition containing a salivation promoting ingredient consisting essentially of from about 4 to about 70% by weight xylitol; and retaining the edible composition for a sufficient time in the oral cavity to promote salivation by the release of xylitol to stimulate salivation.
2. The method of claim 1 wherein the edible composition additionally contains from about 40% to about 85% by weight of a sugar alcohol selected from the group consisting of sorbitol, mannitol and mixtures thereof.
3. The method of claim 1 wherein the edible product is a confectionery.
4. The method of claim 1 wherein the edible product is a chewing gum composition containing a chewing gum base in the amount up to about 56% by weight.
5. The method of claim 4 wherein the chewing gum composition contains a chewing gum base in an amount of about 11% to about 45% by weight.
6. The method of claim 5 wherein the chewing gum base is selected from the group consisting of natural or synthetic elastomers.
7. The method of claim 1 wherein the edible composition contains one or more additional components selected from the group consisting of sweeteners, fillers, plasticizers, softeners, coloring agents, water-soluble artificial sweeteners, dipeptide based sweeteners and mixtures thereof.
8. The method of claim wherein the composition contains a sweetener which is a natural or synthetic compound.
9. The method of claim 8 wherein the sweetener is selected from the consisting of water-soluble sweetening agents, water-soluble artificial sweeteners, dipeptide based sweeteners and mixtures thereof.
10. The method of claim 8 wherein the sweetener is selected from the group consisting of liquid sweeteners, particulate sweeteners and mixtures thereof.
11. The method of claim 1 wherein xylitol is present in the amount of about 4% to about 25% by weight.
12. The method of claim 1 wherein xylitol is present in the amount of about 4% to about 25% by weight and wherein the composition contains about 40% to about 60% by weight of a sugar alcohol selected from the group consisting of sorbitol, mannitol and mixtures thereof.
13. The method of claim for treating xerostomia wherein the xerostomia is caused by factors affecting the brain's control of salivation such as emotions, neurosis and organic diseases.
14. The method of claim 1 for treating xerostomia wherein the xerostomia is caused by factors affecting the automatic outflow pathway such as encephalitis, tumors, cerebrovascular accidents and medications.
15. The method of claim 1 for treating xerostomia wherein the xerostomia is caused by factors affecting the salivary gland such as Sjogren's syndrome, and irradiation.
16. The method of claim 1 for treating xerostomia wherein the xerostomia is caused by factors affecting fluid or electrolyte balance such as dehydration, diabetes, cardiac failure, hypertension, thyroid disease and hormone dysfunction.
17. A candy composition used in the method of claim 1 for treating xerostomia.

18. A chewing gum composition used in the method of claim 1 for treating xerostomia.

19. A chewing gum composition used in the method of claim 4 for treating xerostomia.

20. An edible composition used in the method of claim 11 for treating xerostomia.

21. An edible composition used in the method of claim 12 for treating xerostomia.

* * * * *